United States Patent
Ailinger

(10) Patent No.: US 12,256,899 B2
(45) Date of Patent: Mar. 25, 2025

(54) OVERTUBE, INSERTION APPARATUS HAVING OVERTUBE ATTACHED AND DETACHED THERETO, AND METHOD FOR ATTACHING OVERTUBE TO AND DETACHING OVERTUBE FROM INSERTION APPARATUS

(71) Applicant: OLYMPUS CORPORATION, Tokyo (JP)

(72) Inventor: Robert E. Ailinger, Norwood, MA (US)

(73) Assignee: OLYMPUS CORPORATION, Tokyo (JP)

( * ) Notice: Subject to any disclaimer, the term of this patent is extended or adjusted under 35 U.S.C. 154(b) by 65 days.

(21) Appl. No.: 17/081,436

(22) Filed: Oct. 27, 2020

(65) Prior Publication Data

US 2022/0125279 A1   Apr. 28, 2022

(51) Int. Cl.
*A61B 1/00* (2006.01)

(52) U.S. Cl.
CPC ........ *A61B 1/0016* (2013.01); *A61B 1/00071* (2013.01); *A61B 1/00121* (2013.01); *A61B 1/00135* (2013.01)

(58) Field of Classification Search
CPC .............. A61B 1/0016; A61B 1/00071; A61B 1/00121; A61B 1/00135
See application file for complete search history.

(56) References Cited

U.S. PATENT DOCUMENTS

| | | | |
|---|---|---|---|
| 9,895,051 B2* | 2/2018 | Nishiie | A61B 1/00112 |
| 2012/0029281 A1 | 2/2012 | Frassica et al. | |
| 2012/0289774 A1* | 11/2012 | Oskin | A61B 1/303 600/104 |
| 2016/0175005 A1 | 6/2016 | Dejima | |
| 2016/0296105 A1* | 10/2016 | Ramsey | A61B 1/00154 |
| 2017/0071447 A1 | 3/2017 | Nishiie et al. | |

OTHER PUBLICATIONS

Extended European Search Report dated Feb. 8, 2022 received in 21194639.7.
European Office Action Oct. 9, 2023 received in 21 194 639.7.

* cited by examiner

*Primary Examiner* — Aaron B Fairchild
*Assistant Examiner* — Megan Elizabeth Monahan
(74) *Attorney, Agent, or Firm* — Scully, Scott, Murphy & Presser, P.C.

(57) ABSTRACT

An overtube including: a connector body defining a lumen through which an insertion section of an endoscope is insertable along a longitudinal axis extending through a distal opening and a proximal opening of the lumen; and a connecting mechanism including: a connector movably attached to the connector body, wherein the connector is configured to define a stable equilibrium first position radially away from the longitudinal axis, and to be moved by a radial force from the stable equilibrium first position to a second position radially closer to the longitudinal axis than the first position, and wherein, in the second position, the connector is configured to engage the insertion section to limit relative movement of the connector body and the insertion section along the longitudinal axis while allowing the connector body to be rotated by a drive force relative to the insertion section along the longitudinal axis.

15 Claims, 12 Drawing Sheets

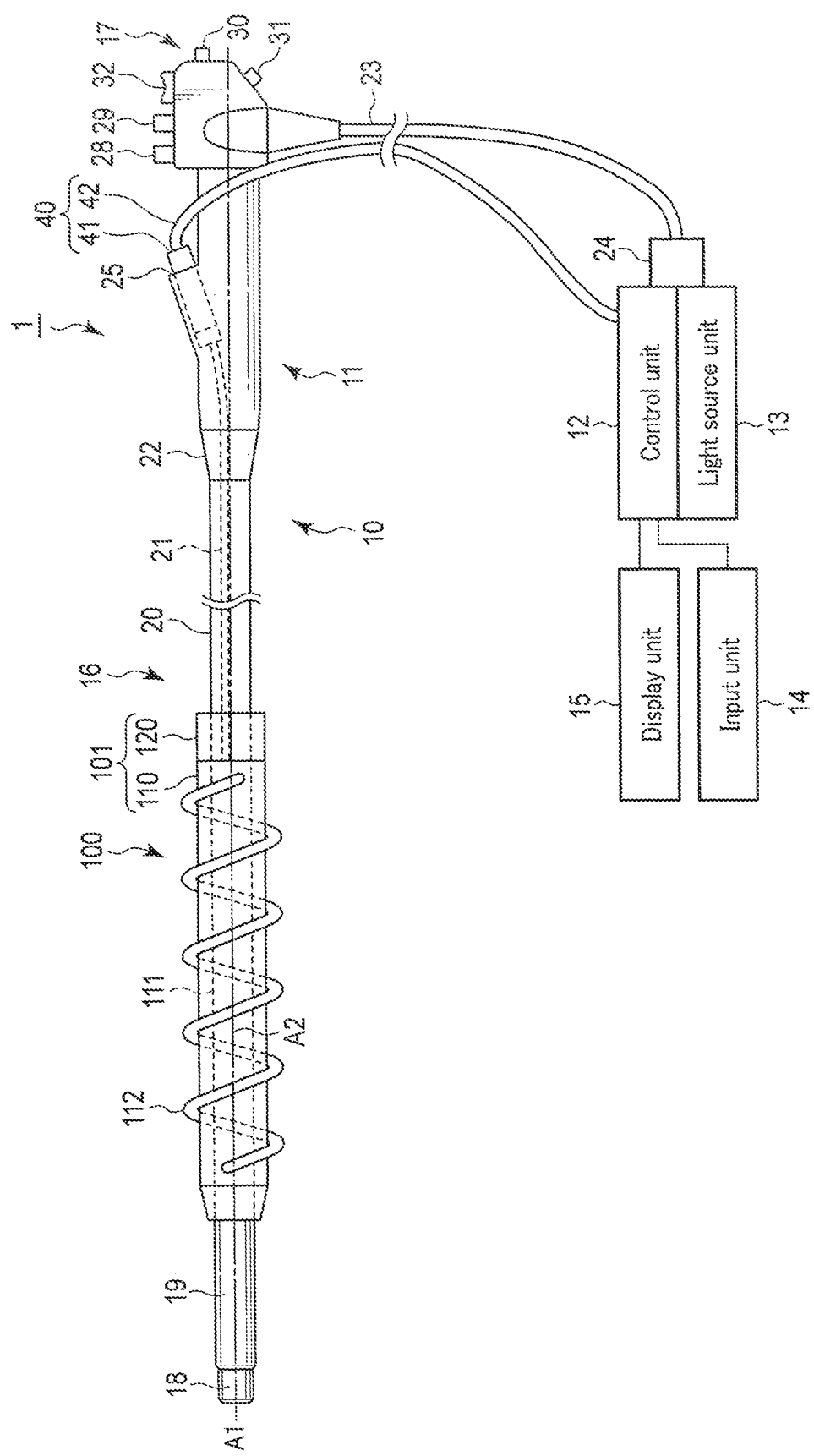
F I G. 1

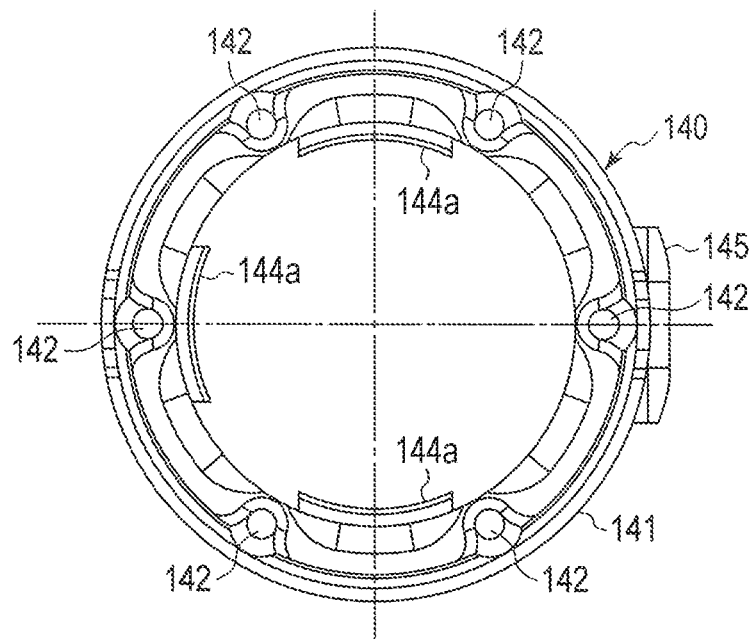
F I G. 12
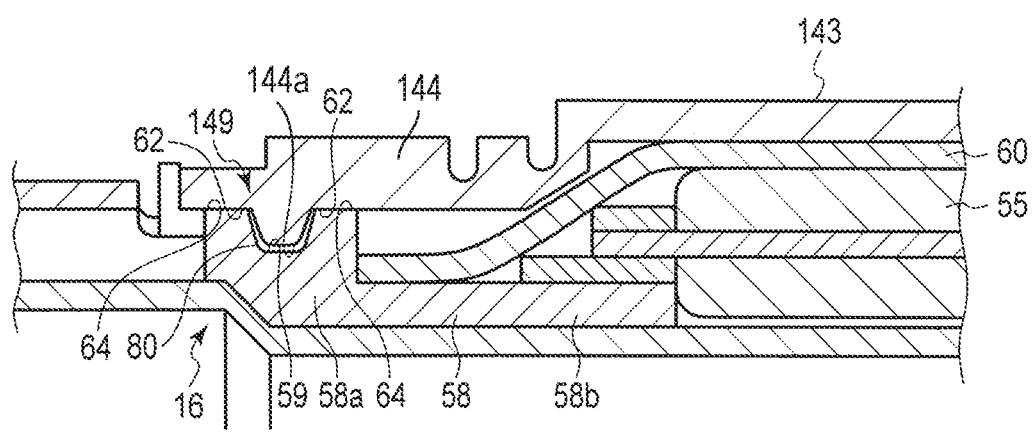
F I G. 13

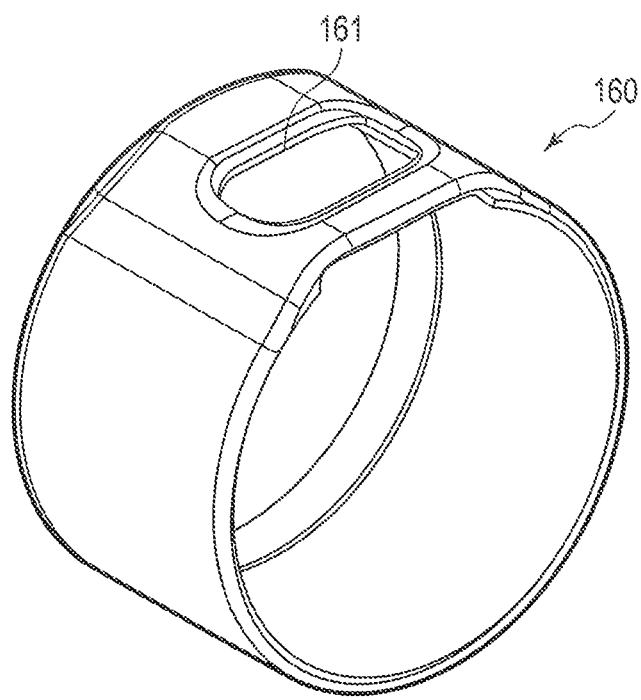
F I G. 14
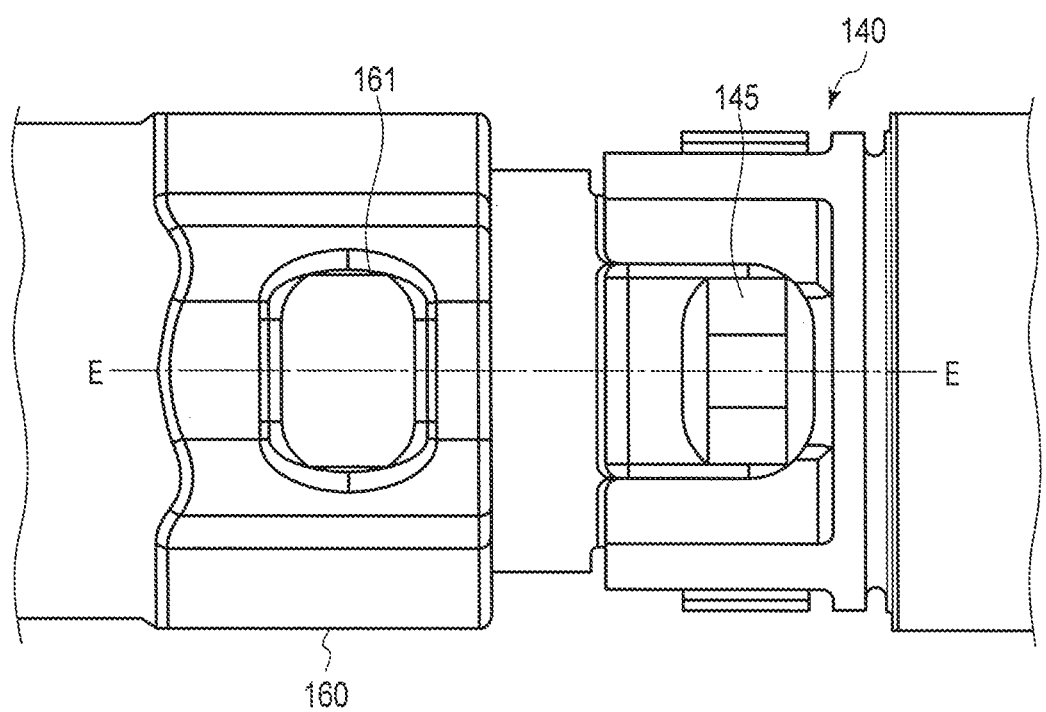
F I G. 15

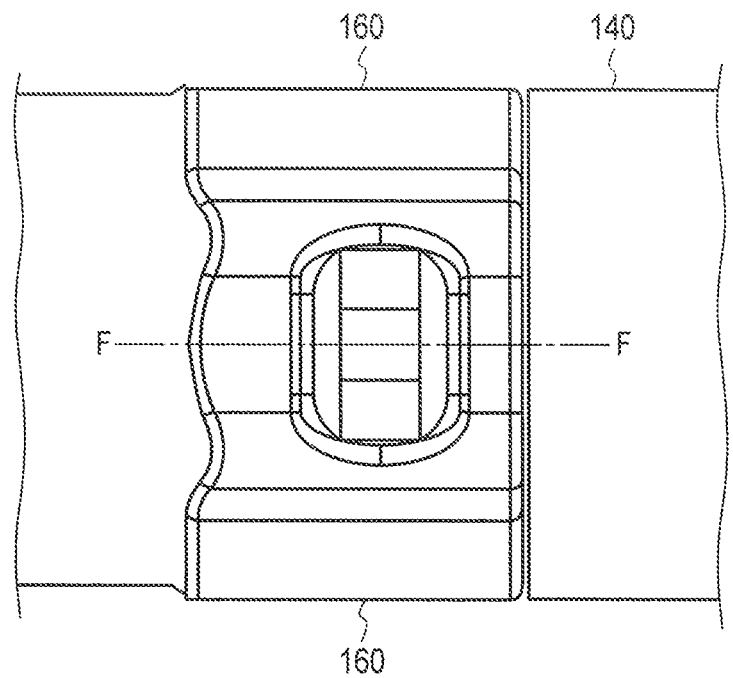
F I G. 16
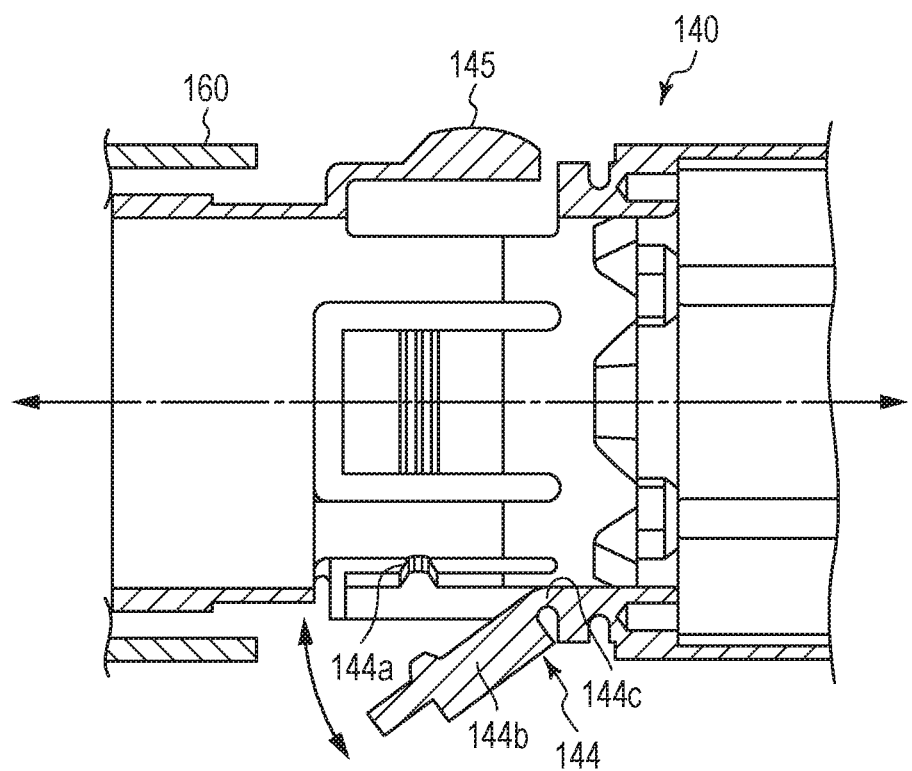
F I G. 17

OVERTUBE, INSERTION APPARATUS HAVING OVERTUBE ATTACHED AND DETACHED THERETO, AND METHOD FOR ATTACHING OVERTUBE TO AND DETACHING OVERTUBE FROM INSERTION APPARATUS

BACKGROUND

Field of the Invention

The present invention relates to an overtube attachable to and detachable from an insertion section of an insertion apparatus, the insertion apparatus having the overtube attached and detached thereto, and a method for attaching the overtube to and detaching the overtube from the insertion apparatus.

Description of the Related Art

An overtube to be attached to and detached from an insertion apparatus, for example, an insertion section of an endoscope, is described in U.S. Patent Application Publication No. US 2017/0071447 A1, published from U.S. patent application Ser. No. 15/362,942, which issued as U.S. Pat. No. 9,895,051 B2. In an attached state of the overtube to the insertion section, the overtube is driven to rotate relative to the insertion section. As the overtube is rotated, the insertion section advances deeper into a cavity as an outer surface of the overtube presses the wall of the cavity in which the insertion section is inserted toward a proximal end.

The overtube can include pawls that can be moved from a first position radially away from a longitudinal axis of the overtube to a second position closer to the longitudinal axis of the overtube to engage a portion of the insertion section of the endoscope arranged in a lumen of the overtube.

During attachment and detachment of the overtube to and from the insertion section of the endoscope, the pawls remain in the first position radially away from the longitudinal axis of the overtube.

In an attached state of the overtube to the insertion section, the pawls are in the second position and are engaged with a circumferential groove provided on the exterior surface of the portion of the insertion section. In the second position, the pawls restrict relative movement of the overtube and the insertion section along the longitudinal axis.

However, during the attachment and detachment of the overtube to and from the insertion section of the endoscope, the pawls, arranged in the first position, can contact an outer surface of the insertion section as the overtube is moved relative to the insertion section along the longitudinal axis. Such contact between the pawls and the outer surface of the insertion section can result in damage to the outer surface of the insertion section.

SUMMARY

According to one embodiment of the invention, an overtube attachable to an insertion section of an endoscope is provided. The overtube comprises: a connector body defining a lumen through which the insertion section is insertable along a longitudinal axis extending through a distal opening and a proximal opening of the lumen; and a connecting mechanism comprising: a connector movably attached to the connector body, wherein the connector is configured to have a stable equilibrium first position radially away from the longitudinal axis, and to be moved by a radial force from the stable equilibrium first position to a second position radially closer to the longitudinal axis than the stable equilibrium first position, and wherein, in the second position, the connector is configured to engage the insertion section to limit relative movement of the connector body and the insertion section along the longitudinal axis while allowing the connector body to be rotated by a drive force relative to the insertion section along the longitudinal axis.

According to another embodiment of the invention, a system comprises: an endoscope comprising an insertion section; and an overtube attachable to the insertion section of the endoscope, the overtube comprising: a connector body defining a lumen through which the insertion section is insertable along a longitudinal axis extending through a distal opening and a proximal opening of the lumen; and a connecting mechanism comprising: a connector movably attached to the connector body, wherein the connector is configured to have a stable equilibrium first position radially away from the longitudinal axis, and to be moved by a radial force from the stable equilibrium first position to a second position radially closer to the longitudinal axis than the stable equilibrium first position, and wherein, in the second position, the connector is configured to engage the insertion section to limit relative movement of the connector body and the insertion section along the longitudinal axis while allowing the connector body to be rotated by a drive force relative to the insertion section around the longitudinal axis.

According to another embodiment of the invention, a method of operating a system comprises: an endoscope comprising an insertion section; and an overtube attachable to the insertion section of the endoscope, the overtube comprising: a connector body defining a lumen through which the insertion section is insertable along a longitudinal axis extending through a distal opening and a proximal opening of the lumen; and a connecting mechanism comprising: a connector movably attached to the connector body, wherein the connector is configured to have a stable equilibrium first position radially away from the longitudinal axis, and to be moved by a radial force from the stable equilibrium first position to a second position radially closer to the longitudinal axis than the stable equilibrium first position, and wherein, in the second position, the connector is configured to engage the insertion section to limit relative movement of the connector body and the insertion section along the longitudinal axis while allowing the connector body to be rotated by a drive force relative to the insertion section around the longitudinal axis, wherein the method comprises inserting the insertion section of the endoscope through the lumen of the connector body along the longitudinal axis; applying the radial force to the connector to move the connector from the stable equilibrium first position radially away from the longitudinal axis to the second position, radially closer to the longitudinal axis than the stable equilibrium first position, to engage the insertion section to limit relative movement of the connector body and the insertion section along the longitudinal axis; and while the connector is in the second position through application of the radial force, applying the drive force to rotate the connector body relative to the insertion section along the longitudinal axis.

BRIEF DESCRIPTION OF THE SEVERAL VIEWS OF THE DRAWINGS

FIG. 1 is a diagram schematically illustrating an endoscope apparatus according to an embodiment of the present invention, that is, an endoscope and a rotation unit attachable thereto.

FIG. 12 is a diagram of the release button main body of the connector as viewed from a proximal end side.

FIG. 13 is a perspective view illustrating a locking collar of the rotation unit.

FIG. 14 is a cross-sectional view illustrating an attached state between the insertion section of the endoscope and the tube of the rotation unit.

FIG. 15 is a top view illustrating the release button main body and the locking collar in an unlocked position.

FIG. 16 is a top view illustrating the release button main body and the locking collar in a locked position.

FIG. 17 is a cross-sectional view taken along line E-E in FIG. 15.

DETAILED DESCRIPTION

Figure 2:
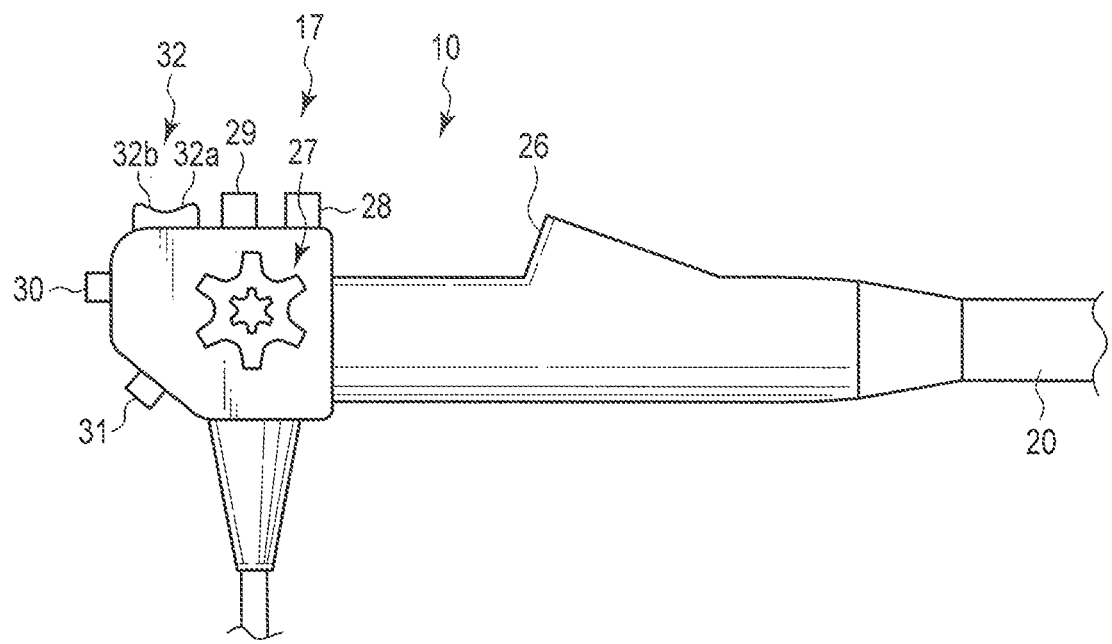
FIG. 2 is a diagram illustrating a side surface on a reverse side of an operation section of the endoscope illustrated in FIG. 1.

Embodiments of the present invention will be explained hereinafter with reference to drawings.

FIG. 1 is a diagram schematically illustrating an endoscope apparatus 1 according to an embodiment of the present invention. The endoscope apparatus 1 includes an endoscope system 10 and an overtube 100.

First, the endoscope system 10 will be described. The endoscope system 10 can include an endoscope 11 as an example of an insertion apparatus, a controller (or a control unit) 12, a light source (or a light source unit) 13, an input device (or an input unit) 14, and a display (or a display unit) 15.

The endoscope 11 can include an insertion section 16 that is elongated, and an operation section 17 provided on a proximal end side of the insertion section 16. The insertion section 16 can have a long tube-shaped member disposed on a distal end side of the endoscope 11. The insertion section 16 can include a distal rigid portion 18, a bending portion 19 provided on the proximal end side of the distal rigid portion 18, and a flexible tube portion 20 provided on the proximal end side of the bending portion 19. The distal rigid portion 18 can include an illumination optical system, an observation optical system, and an image sensor and the like that are not illustrated. The bending portion 19 can be controlled to bend in a desired direction by a user's operation of the operation section 17. The flexible tube portion 20 can be bendable to follow the bending shape in a body cavity into which the insertion section 16 is inserted, for example. A channel 21 can be defined to extend inside the insertion section 16, to accommodate insertion of a drive shaft 51 of a drive mechanism 50 of the endoscope 11. The drive mechanism 50 will be described later.

The operation section 17 can be coupled with the flexible tube portion 20 via a stopper 22. An illumination light fiber and an electrical wire and the like can be arranged from inside of the insertion section 16 to the inside of the operation section 17. The illumination light fiber has a distal end connected with the illumination optical system of the distal rigid portion 18. The electrical wire has a distal end connected with the image sensor of the distal rigid portion 18. The illumination light fiber and the electrical wire can be contained in a universal cable 23 extending from the proximal end side of the operation section 17. A scope connector 24 can be provided at a proximal end of the universal cable 23. The universal cable 23 is configured to be connected with the controller 12 and the light source 13 via the scope connector 24. A drive source attachment port 25 can be provided on the operation section 17, the drive source attachment port 25 communicating with the channel 21 located inside the insertion section 16.

The controller 12 is electrically connected with the endoscope 11, the light source 13, the input device 14, and the display 15. The controller 12 controls operations of the endoscope 11 and peripheral devices (such as the light source 13 and a drive source 40 described later) connected thereto. The controller 12 can include an image processor that is not illustrated. The light source 13 supplies illumination light to the illumination optical system arranged in the distal rigid portion 18 via the illumination light fiber. The input device 14 can include devices such as a keyboard and a mouse, and receives instructions inputted by the user. The display 15 can include a liquid crystal display, to display images acquired by the image sensor of the distal rigid portion 18 and subjected to image processing by the controller 12, and operating information.

FIG. 2 is a diagram illustrating a side surface on a reverse side of the operation section 17 of the endoscope 11 illustrated in FIG. 1. The operation section 17 can include a treatment tool insertion port 26 communicating with a treatment tool channel (not illustrated) extending inside the insertion section 16. The treatment tool insertion port 26 can be arranged side by side with the drive source attachment port 25 illustrated in FIG. 1. A treatment tool, such as an ultrasonic probe and biopsy forceps can be inserted into the treatment tool insertion port 26.

As illustrated in FIG. 2, the side surface of the operation section 17 can be provided with a bending operation knob 27 to receive an input of an operation to bend the bending portion 19 in a desired direction. Inside the operation section 17, a proximal end of a bending wire (not illustrated) to bend the bending portion 19 can be connected with a shaft coupled with the bending operation knob 27. The distal end of the bending wire can be connected with the distal end portion of the bending portion 19. When the user rotates the bending operation knob 27, the bending wire coupled therewith is pulled, and thereby the bending portion 19 is bent.

The operation section 17 can be provided with various types of switches 28, 29, 30, and 31, such as an air/water feed switch, a suction switch, an imaging switch, and another changeover switch to change over a predetermined function. The operation section 17 can also be provided with a rotation operation input switch 32 to output a signal for rotating the overtube 100 around a central axis A1 of the insertion section 16 to the controller 12. When the user presses a position indicated with a reference numeral 32a, for example, to incline the switch 32, the rotation operation input switch 32 outputs a signal to rotate the overtube 100 in a first direction (for example, a clockwise direction) to the controller 12. When the user presses a position indicated with a reference numeral 32b to incline the switch 32, the rotation operation input switch 32 outputs a signal to rotate the overtube 100 in a second direction (for example, a counterclockwise direction) opposite to the first direction to the controller 12.

Next, with reference to FIG. 1, a drive source 40 to rotation-drive the overtube 100 around the central axis A1 can be attached to the drive source attachment port 25. The drive source 40 can include a motor main body 41 including a rotary shaft, and a motor cable 42 extending from the motor main body 41. The external circumference of the motor main body 41 can be held on the drive source attachment port 25 with a holder ring that is not illustrated. The rotary shaft of the motor main body 41 can be connected with the drive shaft 51 of the drive mechanism 50 described later. The proximal end of the motor cable 42 is electrically connected with the controller 12.

Figure 6:
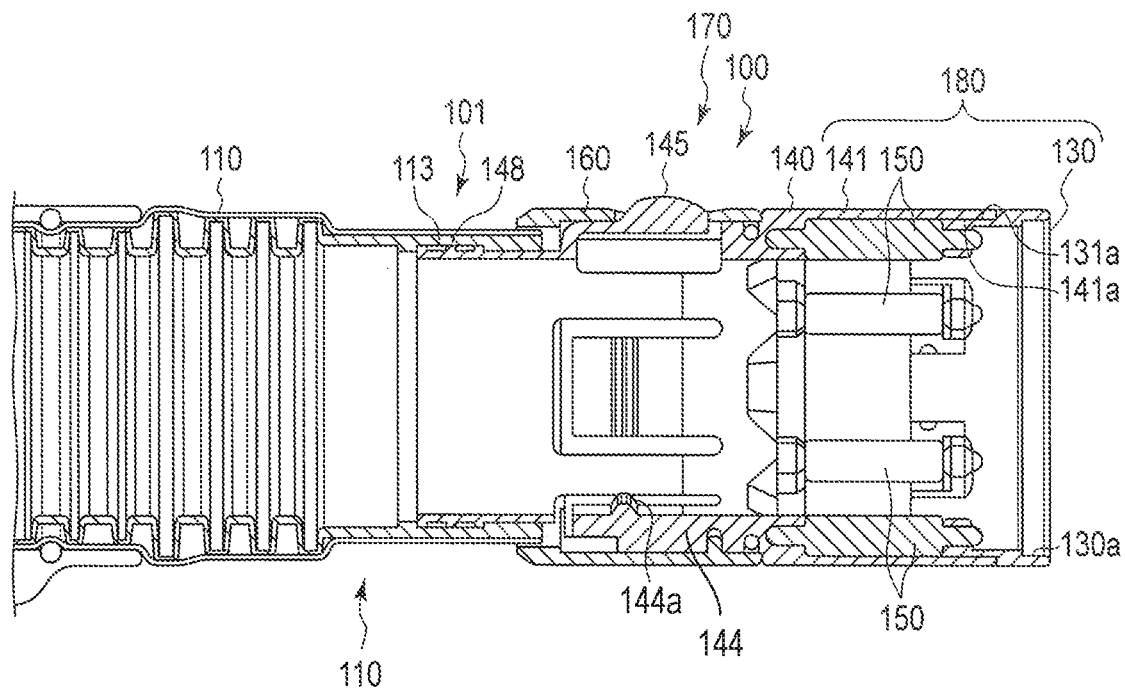
FIG. 6 is a cross-sectional view illustrating the tube of the rotation unit.

Next, with reference to FIG. 1 and FIG. 6, the overtube 100 will be described. The overtube 100 can include a rotatable tube 101, the rotatable tube 101 can include a tube main body 110 that is substantially cylindrical in shape and a connector 120 provided on the proximal end side of the tube main body 110. The rotatable tube 101 can be a disposal tube that is detachably attached to the external circumferential surface of the insertion section 16. The connector 120 is provided to attach the rotatable tube 101 at a proximal end side of the rotatable tube 101 onto the insertion section 16.

The rotatable tube 101 can extend along a longitudinal axis A2 from a distal end opening and a proximal end opening of a lumen 111 defined by the rotatable tube 101. When the rotatable tube 101 is attached onto the insertion section 16, the longitudinal axis A2 can be coaxial with the rotation central axis A1 described above. The insertion section 16 can be inserted and retracted through the lumen 111 of the rotatable tube 101.

The internal circumferential surface of the rotatable tube 101 defining the lumen 111 can have a shape that is substantially fitted to the shape of the external circumferential surface of the insertion section 16 when the rotatable tube 101 is attached by the connector 120 onto the insertion section 16.

The tube main body 110 can be a flexible tube including a corrugated external surface. The tube main body 110 can be made of a resin material such as polyurethane. At least part of the external circumferential surface of the tube main body 110 can be provided with a spiral fin 112 that is provided in a clockwise spiral manner as viewed from the proximal end direction. The spiral fin 112 can be fixed to the tube main body 110 by bonding or welding, or formed as one unitary piece with the tube main body 110, and can radially protrude from the external circumferential surface of the tube main body 110. The spiral fin 112 can be solid or hollow, or may be filled with fluid. The spiral fin 112 can be deformable such that the spiral fin 112 has a reduced shape to easily pass through a narrow body cavity when the spiral fin 112 advances inside the narrow body cavity and the spiral fin 112 has an enlarged shape when the spiral fin 112 performs a desired rotation advance after passing through the narrow body cavity. The spiral fin 112 can be formed of, for example, polyurethane, thermoplastic elastomer (TPE), silicone, tetrafluoroetheylene (TFE), medical grade stainless steel, tantalum, titanium, or nickel-titanium alloy or the like.

Figure 3:
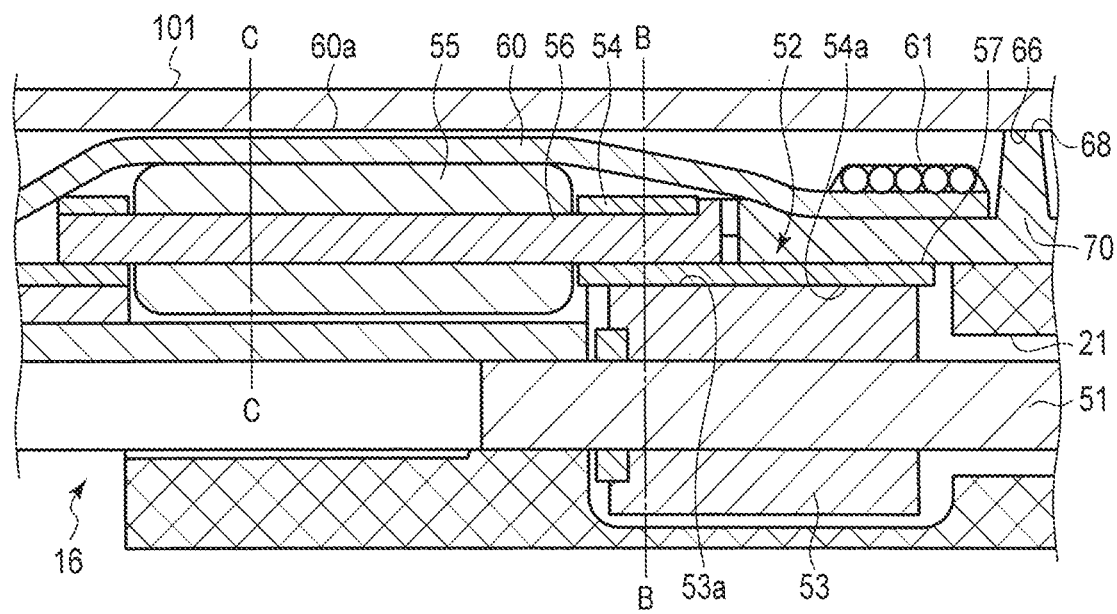
FIG. 3 is a cross-sectional view illustrating a drive unit provided in an insertion section of an endoscope main body, and configured to rotation-drive a tube of the rotation unit.
Figure 4:
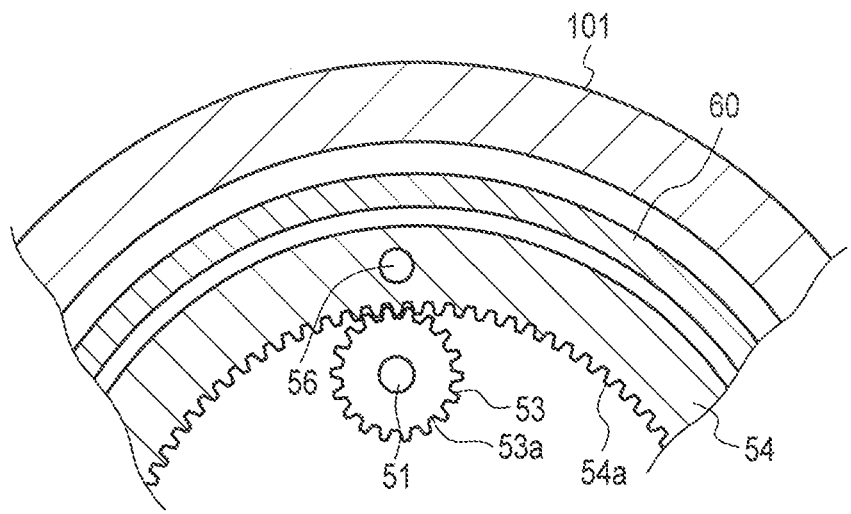
FIG. 4 is a cross-sectional view taken along line B-B of FIG. 3.

Next, the drive mechanism 50 of the endoscope 11 to rotation-drive the rotatable tube 101 of the overtube 100 will be described. FIG. 3 is a cross-sectional view illustrating the drive mechanism 50 provided in the insertion section 16 of the endoscope 11. FIG. 4 is a cross-sectional view taken along line B-B of FIG. 3. The drive mechanism 50 can include the drive shaft 51 and a gear box 52. The gear box 52 can include a rotary gear 53, an internal gear 54, and a drive roller 55.

As illustrated in FIG. 1 and FIG. 3, the proximal end of the drive shaft 51 is connected with the rotary shaft of the motor main body 41. The drive shaft 51 can be arranged in the channel 21 extending inside the insertion section 16. The drive shaft 51 can have, for example, a multi-layer structure in which metal wires that are woven in a cylindrical net shape are superimposed, or can be formed of multi-layered wires in which clockwise wires and counterclockwise wires are superimposed, and has rotation followability to the motor main body 41 and flexibility.

The distal end of the drive shaft 51 can be provided with the rotary gear 53 of the gear box 52. The drive shaft 51 can rotate the rotary gear 53, when a rotational force around the longitudinal axis of the drive shaft 51 is applied to the proximal end of the drive shaft 51. External teeth 53a of the rotary gear 53 are meshed with internal teeth 54a of the internal gear 54 provided on the external circumference of the insertion section 16. A shaft 56 of the drive roller 55 is attached to the internal gear 54. Accordingly, the drive force from the motor main body 41 of the drive source 40 is transmitted from the drive shaft 51, to rotation-drive the rotary gear 53, the internal gear 54, and the drive roller 55 of the gear box 52.

The internal gear 54 and the drive roller 55 can be arranged to be shifted from each other in the longitudinal axis direction. With this structure, a space is formed on the external circumferential surface of the internal gear 54 in a range not exceeding the height of the drive roller 55. A bearing portion 70 can be provided in the space in the present embodiment. The bearing portion 70 is provided on a base member 57, and serves as an opening portion that is slidably fitted on the external circumferential surface of the proximal end portion of the internal gear 54. In other words, in the longitudinal axis direction of the endoscope 11, the bearing portion 70 is arranged to be superimposed on the mesh portion between the external teeth 53a of the rotary gear 53 and the internal teeth 54a of the internal gear 54.

The internal gear 54 and the drive roller 55 can be covered with a cover 60 at the external circumferential surface of the insertion section 16. The cover 60 is provided with a radial protruding portion 60a formed on its external surface by covering the drive roller 55. The cover 60 can be a waterproof sheet member providing a barrier or a seal to protect the internal gear 54, the drive roller 55, and other members of the endo scope 11 arranged inside thereof. The cover 60 maintains watertightness of the inside of the endoscope 11 (insertion section 16), and prevents infiltration of water or other fluids. The cover 60 can be fixed to the external circumferential surface of the insertion section 16 with a cover fixing material 61. The cover 60 can be bonded by spool bonding with the cover fixing material 61.

Figure 5:
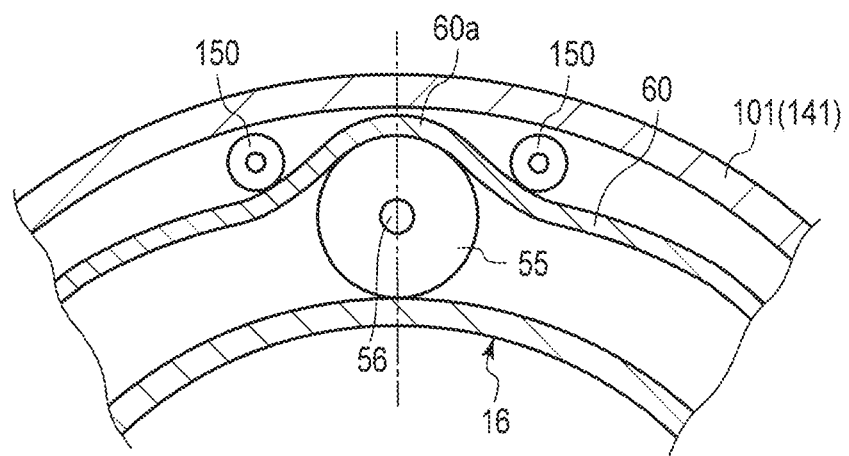
FIG. 5 is a cross-sectional view taken along line C-C of FIG. 3.

FIG. 5 is a cross-sectional view taken along line C-C of FIG. 3. As described above, the external circumferential surface of the drive roller 55 of the drive mechanism 50 can be covered with the cover 60 outside the insertion section 16 in the radial direction. Outside the cover 60 in the radial direction, rollers 150 of the connector 120, described later, can be arranged one by one with the protruding portion 60a interposed therebetween, to abut against the external circumferential surface of the cover 60. The rollers 150 can also abut against the internal circumferential surface of a connector body 140 of the connector 120 of the rotatable tube 101 described later, outside the insertion section 16 in the radial direction.

When the drive mechanism 50 is driven, the drive force from the drive source 40 is transmitted to the drive roller 55, via the drive shaft 51, the rotary gear 53 and the internal gear 54 of the gear box 52. In this manner, the drive roller 55 is rotated around the rotational axis A1. The drive roller 55 and the rollers 150 rotate on the cover 60 to reduce friction caused by the cover 60. Because the cover 60 is fixed to the external circumferential surface of the insertion section 16, the cover 60 is not rotated with respect to the insertion section 16. By contrast, the two rollers 150 maintain the drive roller 55 between the rollers 150, and thereby the drive roller 55 transmits the rotational movement of the internal gear 54 to the rotatable tube 101 beyond the cover 60. Thus, the drive force from the drive source 40 is transmitted from the drive mechanism 50 to the overtube 100, and the overtube 100 is rotation-driven around the rotational axis A1. For example, when inspection of the small intestine or the large intestine is performed, the overtube 100 advances while pressing the folds of the small intestinal wall and the large intestinal wall abutting against the spiral fin 112 of the rotating tube main body 110 toward the proximal end, to assist the insertion of the insertion section 16.

As an alternative to rollers 150, cams (not illustrated) can be provided. When the drive mechanism 50 is driven, the drive force from the drive source 40 is transmitted to the drive roller 55, via the drive shaft 51, the rotary gear 53 and the internal gear 54 of the gear box 52. In this manner, the drive roller 55 is rotated around the rotational axis A1. Because the cover 60 is fixed to the external circumferential surface of the insertion section 16, the cover is not rotated with respect to the insertion section 16. By contrast two cams maintain the drive roller 55 between the two cams, and thereby the drive roller 55 transmits the rotational movement of the internal gear 54 to the rotatable tube 101 beyond the cover. Thus the drive force from the drive source 40 is transmitted from the drive mechanism 50 to the overtube 100, and the overtube 100 is rotation-driven around the rotational axis A1.

The internal circumferential surface of the rotatable tube 101 can be provided with a bearing surface 66 that is located on the proximal end side beyond the drive roller 55 transmitting the drive force as illustrated in FIG. 3, and engaged with a bearing surface 68 provided on the external circumferential surface of the base member 70. The bearing surfaces 66 and 68 are circumferential surfaces. An internal diameter of the bearing surface 66 is formed slightly larger than the external diameter of the bearing surface 68 such that the bearing surface 66 is slidable with respect to the bearing surface 68 with rotation of the rotatable tube 101 with respect to the insertion section 16. Specifically, the bearing surfaces 66 and 68 function as a radial movement restricting mechanism restricting movement of the rotatable tube 101 in the radial direction of the insertion section 16.

Next, the connector 120 of the rotatable tube 101 of the overtube 100, as shown in FIG. 1, will be described. FIG. 6 is a cross-sectional view illustrating the rotatable tube 101 of the overtube 100. The connector 120 can include an annular proximal end sleeve 130, the connector body 140, and the rollers 150 (or the cams) described above. The proximal end sleeve 130 can be engaged with a proximal end of the connector body 140. The proximal end sleeve 130 and the connector body 140 can rotatably hold the rollers 150 (or the cams). The connector body 140 can also be engaged with a locking collar 160, described below, that is slidable in the longitudinal axis direction of the rotatable tube 101.

Figure 7:
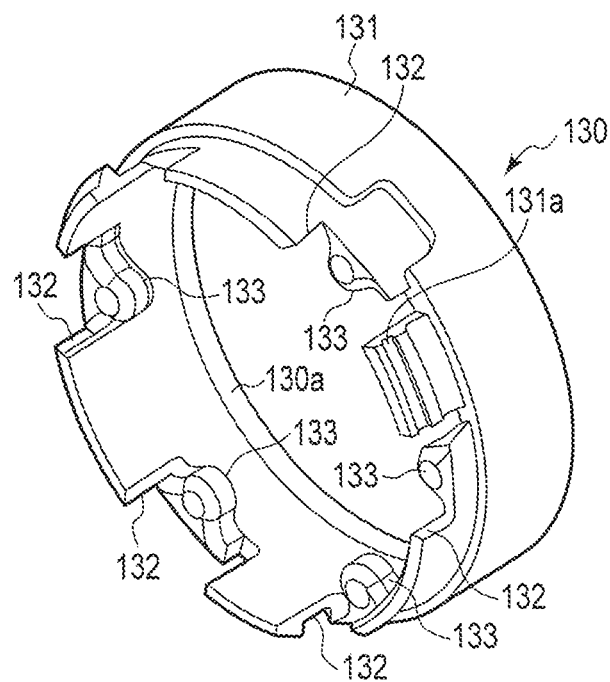
FIG. 7 is a perspective view illustrating a proximal end sleeve of a connector.
Figure 8:
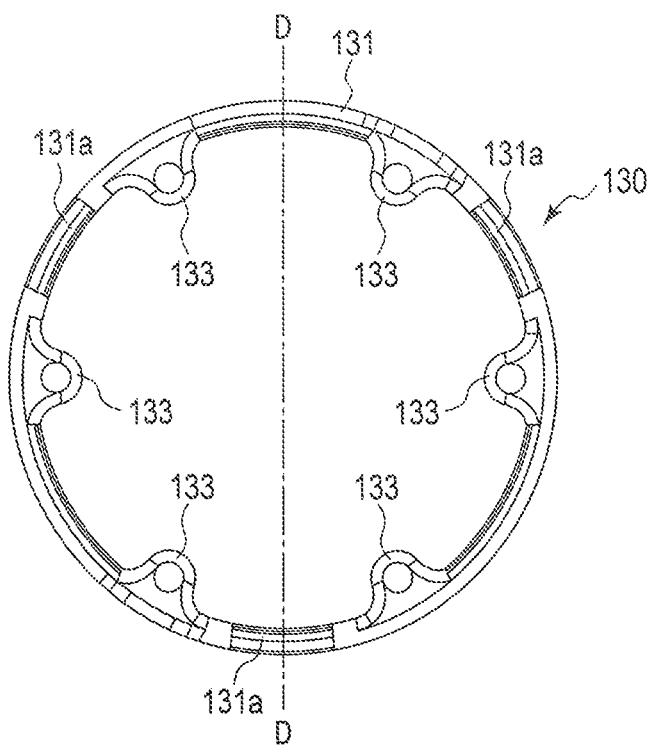
FIG. 8 is a diagram of the proximal end sleeve of the connector as viewed from a distal end side.
Figure 9:
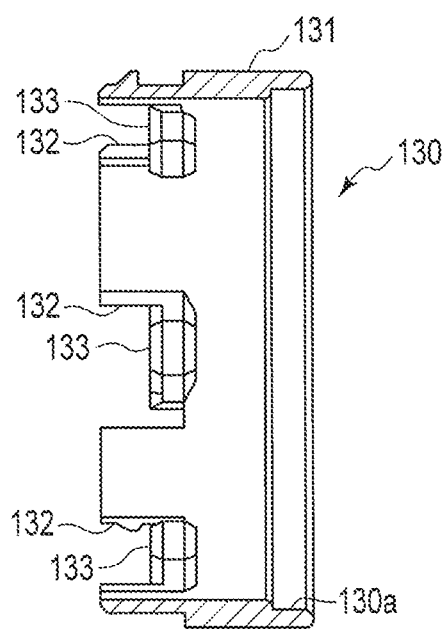
FIG. 9 is a cross-sectional view taken along line D-D of FIG. 8.

FIG. 7 to FIG. 9 are a perspective view of the proximal end sleeve 130, a front view thereof as viewed from the distal end side, and a cross-sectional view thereof taken along line D-D of FIG. 8, respectively. The proximal end sleeve 130 can include six cutout portions 132 formed in the distal end portion of a cylindrical wall 131, and six roller holding portions 133 arranged in the respective cutout portions 132. The roller holding portions 133 radially protrude from the internal circumferential surface of the proximal end sleeve 130, to hold the rollers 150 substantially parallel with the longitudinal axis direction of the insertion section 16 when the rotatable tube 101 is attached onto the insertion section 16. One end portions of the six rollers 150 are held to be rotatable around the axis by the corresponding roller holding portions 133, respectively. Three engaging portions 131a, each having an uneven shape on the external surface thereof, are formed on the distal end side of the cylindrical wall 131 of the proximal end sleeve 130. These engaging portions 131a are engaged with respective corresponding engaging portions 141a formed on the internal circumference of a large-diameter portion 141 of the connector body 140 described later. A large-diameter internal circumferential surface 130a provided on the internal circumference of the proximal end sleeve 130 on the proximal end side has a structure corresponding to the bearing surface 66 (see FIG. 3) described above, and slidably fitted with a surface of the insertion section 16 corresponding to the bearing surface 68.

Figure 10:
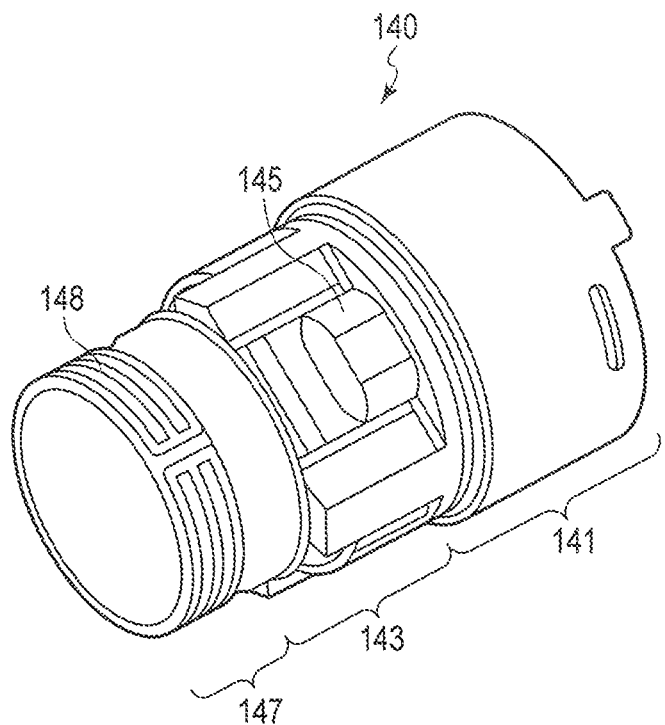
FIG. 10 is a perspective view illustrating a release button main body of the connector.
Figure 11:
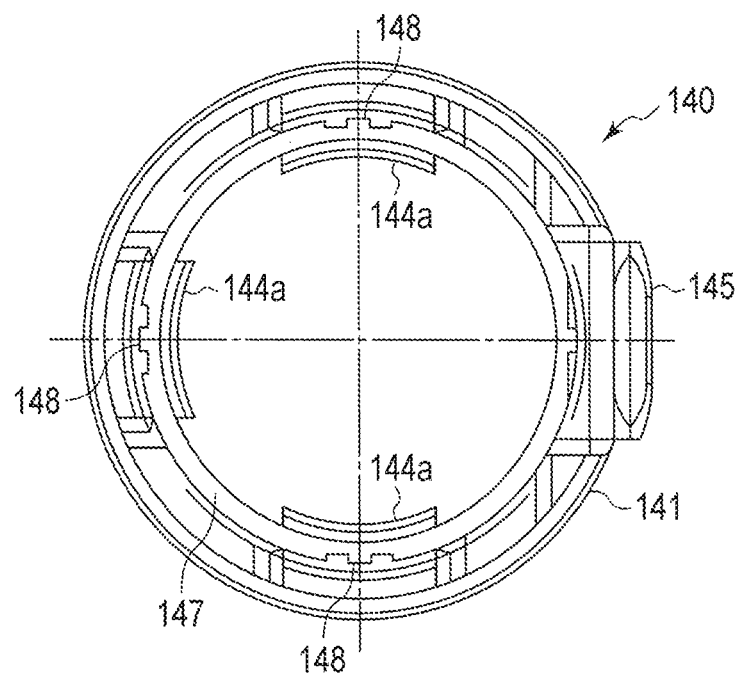
FIG. 11 is a diagram of the release button main body of the connector as viewed from the distal end side.

FIGS. 10-12 are a perspective view of the connector body 140, a front view thereof as viewed from the distal end side, and a back view thereof as viewed from the proximal end side, respectively.

The connector body 140 can include the large-diameter portion 141 on the proximal end side, a medium-diameter portion 143 in the middle, and a small-diameter portion 147 on the distal end side.

An external diameter of the large-diameter portion 141 can be larger than an external diameter of the medium-diameter portion 143. Further, the external diameter of the medium-diameter portion 143 can be larger than an external diameter of the small-diameter portion 147.

An internal diameter of the large-diameter portion 141 can be larger than internal diameters of the medium-diameter portion 143 and the small-diameter portion 147, and the internal diameters of the medium-diameter portion 143 and the small-diameter portion 147 can be substantially equal. Further, the internal circumferential surfaces of the large-diameter portion 141, the medium-diameter portion 143, and the small-diameter portion 147 form part of the lumen 111 in the rotatable tube 101, and have a shape that allows for a distal portion of the external circumferential surface of the insertion section 16 to be inserted and passed through the lumen 111 and a proximal portion of the external circumferential surface of the insertion section 16 to be arranged within the lumen 111.

The large-diameter portion 141 can be provided with six roller holding portions 142 to hold the other end portions of the six rollers 150. The roller holding portions 142 hold the respective rollers 150 rotatably in the axial direction, together with the roller holding portions 133 of the proximal end sleeve 130. The large-diameter portion 141 together with the proximal end sleeve 130 and the rollers 150 form a rotational engagement mechanism 180 (as shown in FIG. 6) to rotatably engage the rotatable tube 101 to the insertion section 16.

As described above, the rotational engagement mechanism 180 is configured to be engaged with the protruding portion 60a formed on the cover 60 and receive the drive force from the drive mechanism 50. The rotational engagement mechanism 180 is provided on the rotatable tube 101, receives the drive force from the drive mechanism 50, and is rotated with respect to the insertion section 16 inserted through the lumen 111 of the tube main body 110.

As shown in FIGS. 13 and 17-21, the connector body 140 can be provided with one or more connectors 144 movably attached to the medium-diameter portion 143 of the connector body 140. Each of the one or more connectors 144 can be movably attached to the medium-diameter portion 43 to maintain the each of the one or more connectors 144 in a stable equilibrium first position radially away from the longitudinal axis A2 of the rotatable tube 101 and to be moved, by applying an external force thereon, to a second position, radially closer to the longitudinal axis A2 of the rotatable tube 101 than the stable equilibrium first position, to engage with grooves (concave portions) 59 arranged in the insertion section 16, described later, to form a locking mechanism 170. The external force can include, for example, an external radial force towards the longitudinal axis A2.

In one configuration, the stable equilibrium first position of each of the connectors 144 can be set so that the connectors 144, collectively, provide sufficient clearance and do not contact the distal portion of the insertion section 16 as the distal portion of the insertion section 16 is moved along the longitudinal axis A2 through the lumen 111 of the rotatable tube 101, and do not contact the proximal portion of the insertion section 16 that is within the lumen 111 when the rotational engagement mechanism 180 is moved into position to engage with the protruding portion 60a formed on the cover 60 to receive the drive force from the drive mechanism 50.

In another configuration, the stable equilibrium first position of each of the one or more connectors 144 can be set to be substantially the same distance radially away from the longitudinal axis A2 so that the one or more connectors 144 provide sufficient clearance and do not contact the distal portion of the insertion section 16 as the distal portion of the insertion section 16 is moved along the longitudinal axis A2 through the lumen 111 of the rotatable tube 101, and do not contact the proximal portion of the insertion section 16 that is within the lumen 111 when the rotational engagement mechanism 180 is moved into position to engage with the protruding portion 60a formed on the cover 60 to receive the drive force from the drive mechanism 50.

Figure 19:
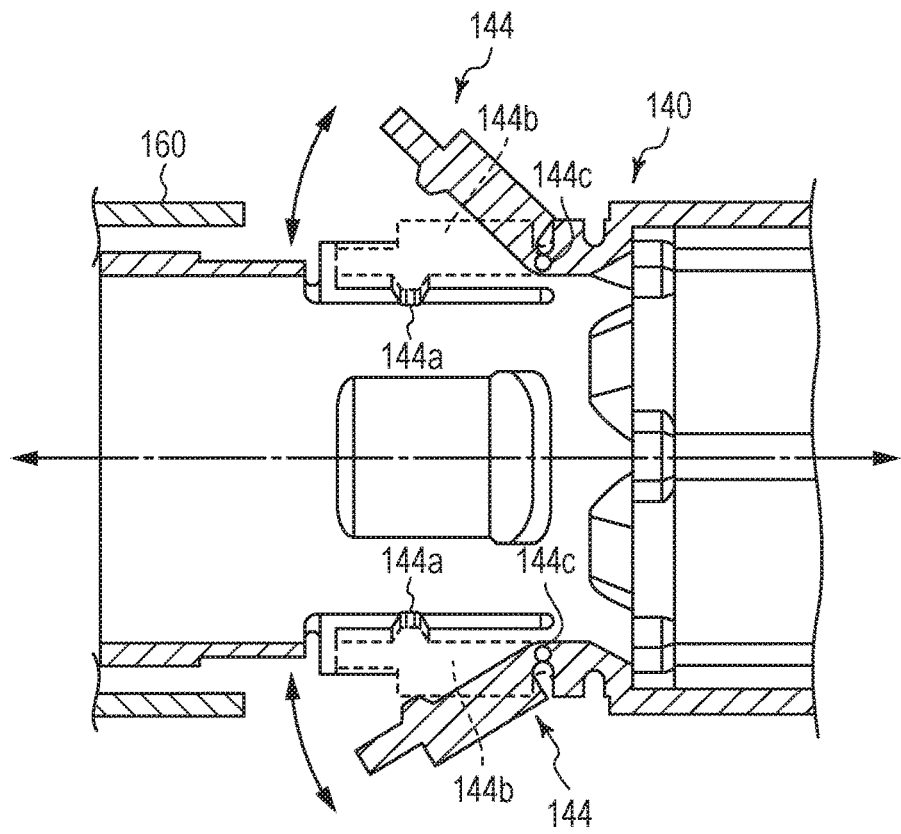
FIG. 19 is a cross-sectional view in a direction orthogonal to the cross section illustrated in FIG. 17.

In more detail, each of the connectors 144 can include a locking surface 144a. In the stable equilibrium first position, as shown in FIGS. 17 and 19, the locking surface 144a is arranged at least a predetermined distance radially away from the longitudinal axis A2 to provide sufficient clearance to allow the distal portion of the insertion section 16 to be moved along the longitudinal axis A2 through the lumen 111 without contacting the locking surface 144a.

In the present embodiment, each of the one or more connectors 144 can be biased to return to the stable equilibrium first position further away from the longitudinal axis A2 than the second position. Thereby, upon removal of the external force, the each of the one or more connectors 144 move from the respective second positions to the stable equilibrium first position to provide the sufficient clearance for the distal portion of the insertion section 16 to be moved along the longitudinal axis A2 through the lumen 111 of the rotatable tube 101 without contacting the distal portion of the insertion section 16.

An example of a connector 144 that can be biased to return to the stable equilibrium first position will be described. The connector 144 can include a tab 144b including the locking surface 144a. The connector 144 can further include a hinge 144c configured to movably attach the tab 144b to the connector body 140. The hinge 144c is configured to bias the tab 144b to return to the stable equilibrium first position radially away from the longitudinal axis A2. Further, the tab 144b is configured to be moved by the external force to pivot along the hinge 144c from the stable equilibrium first position to the second position to engage the locking surface 144a with the corresponding portion of the insertion section 16 to limit movement of the connector body 140 relative to the insertion section 16 along the longitudinal axis A2 while allowing the connector body 140 to rotate relative to the insertion section 16 around the longitudinal axis A2.

The tab 144b and the hinge 144c can be formed from a single material as a living hinge. In addition, the tab 144b, the hinge 144c and the connector body 140 can be formed from a single material as the living hinge. The living hinge can be formed as a flat hinge where the tab 144b and the connector body 140 are formed to be thicker and more rigid than the hinge 144c. The tab 144b and the hinge 144c can be formed by molding. Further, the hinge 144c can be formed by, for example, thinning or cutting, to be flexible and to bias the tab 144b to return to the stable equilibrium first position. The hinge 144c is not required to be thinner than the tab 144B, as long as the hinge 144C is biased to return to the stable equilibrium first position. Further, other embodiments of living hinges are contemplated. For example, the tab 144b and the hinge 144c can be formed as a double hinge, a butterfly hinge or a bi-stable hinge.

Figure 21:
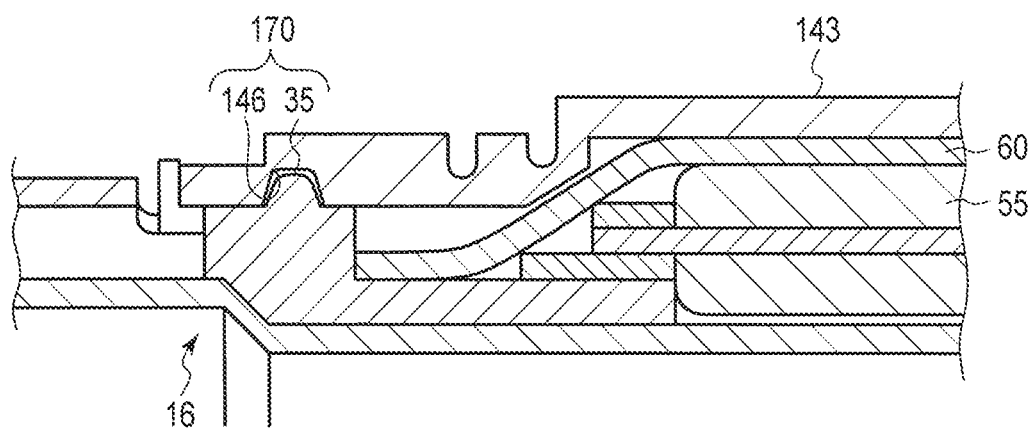
FIG. 21 is a cross-sectional view illustrating an attached state between the insertion section of the endoscope and the tube of the rotation unit.

In the example described above where the connector 144 includes the tab 144b and the hinge 144c, the tab 144b can further including the locking surface 144a. The locking surface 144a, in both the stable equilibrium first position and the second position, can be a surface of the connector 144 that is radially closest to the longitudinal axis A2. The locking surface 144a can be formed as a convex protrusion, as shown in FIG. 13. Alternatively, the locking surface 144a can define a concave groove 146, as shown in FIG. 21. Further, the insertion section 16 can define one of a concave groove 59, as shown in FIG. 13, to receive the convex protrusion of the locking surface 144a of the tab 144b. Alternatively, the insertion section 16 can form a convex protrusion, as shown in FIG. 21, to be received by the concave groove of the locking surface 144a.

Based on the above-described convex protrusion and concave groove structure, the tab 144b can be moved by the external force to pivot along the hinge 144c from the stable equilibrium first position to the second position to engage the one of the convex protrusion and the convex groove forming the locking surface 144a with one of the concave groove and the convex protrusion defined by the insertion section, respectively, to engage the locking surface 144a with the insertion section 16 to limit movement of the connector body 140 to rotate relative to the insertion section 16 around the longitudinal axis A2.

In one configuration shown in FIGS. 13 and 17-21, the hinge 144c can be arranged to be closer to the rotational engagement mechanism 180 along the longitudinal axis A2 than the locking surface 144a. In an alternative configuration shown in FIG. 22, the locking surface 144a can be arranged to be closer to the rotational engagement mechanism 180 along the longitudinal axis A2 than the hinge 144c.

Other mechanisms by which the one or more connectors 144 can be moved to and be maintained in stable equilibrium in the stable equilibrium first position are also considered to be covered by the present disclosure. For example, each of the one or more connectors can be formed in a cantilever manner having the stable equilibrium first position and to be movable by the external force into the second position to engage the insertion section 16 to limit movement of the connector body 140 to rotate relative to the insertion section 16 around the longitudinal axis A2.

The medium-diameter portion 143 can also be provided with the release button 145 radially protruding from an external surface thereof. As illustrated in FIG. 10, the release button 145 can be supported by the medium-diameter portion 143 in a cantilever manner. This structure enables the release button 145 to move in the substantially radial direction when the user pushes the release button 145 from above or slides the locking collar 160 to a position on the release button 145. The release button 145 also forms the locking mechanism 170 by being engaged with an opening 161 of the locking collar 160.

The small-diameter portion 147 can include engaging portions 148 formed on the external circumferential surface of the small-diameter portion 147. The engaging portions 148 can be attached to corresponding engaging portions 113 formed on the internal circumferential surface of the proximal end portion of the tube main body 110.

Next, an attached state between the insertion section 16 of the endoscope 11 and the rotatable tube 101 of the overtube 100, in which the connectors 144 are in the second position, will be described.

FIG. 13 is a cross-sectional view illustrating the attached state between the insertion section 16 and the rotatable tube 101. In the insertion section 16, the distal end side of the drive roller 55 can be provided with an annular receiving member 58 to receive the connectors 144 of the connector body 140 of the connector 120. The receiving member 58 can be part of the gear box 52, and serves as a fixed part that is not rotated with respect to the insertion section 16. The receiving member 58 can be arranged on the external circumferential surface of the insertion section 16, and can include a distal end side portion 58a having a larger radial height, and a proximal end side portion 58b having a radial height smaller than that of the distal end side portion 58a. The distal end side portion 58a can be provided with the grooves 59 recessed in the radial direction and extending along the circumferential direction of the external circumferential surface of the insertion section 16. The distal end side of the cover 60 is fixed to the proximal end side portion 58b.

As described above, the rotatable tube 101 of the overtube 100 can include one or a plurality of the connectors 144 provided in the medium-diameter portion 143 of the connector body 140. Specifically, the connectors 144 can be arranged on the distal end side beyond the proximal end sleeve 130, the rollers 150, and the large-diameter portion 141 of the connector body 140 that form the rotational engagement mechanism 180 in the rotatable tube 101.

As shown in FIGS. 17 and 19, each of the connectors 144 can be moved, by application of the external force, to the second position to engage a corresponding portion of the insertion section 16 that is within the lumen 111 when the rotational engagement mechanism 180 is moved into position to engage with the protruding portion 60a formed on the cover 60 to receive the drive force from the drive mechanism 50. In the second position, the one or more connectors 144 engage the corresponding portion of the insertion section 16 to limit relative movement of the connector body 140 and the insertion section 16 along the longitudinal axis A2 while allowing the connector body 140 to be rotated by the drive force relative to the insertion section 16 around the longitudinal axis A2.

It is noted that engagement of the each of the connectors 144 with the corresponding portion of the insertion section 16 can include continuous contact or intermittent contact between the each of the connectors 144 and the corresponding portion of the insertion section 16 as the rotatable tube 101 is driven to rotate by the drive force from the drive mechanism 50 as long as such contact limits relative movement of the connector body 140 and the insertion section 16 along the longitudinal axis A2 while allowing the connector body 140 to be rotated by the drive force relative to the insertion section 16 along the longitudinal axis A2.

The locking surfaces 144a of the connectors 144 can protrude from the internal surface of the medium-diameter portion 143 in the internal diameter direction, and can be engaged with the grooves 59 formed in the receiving member 58. The locking surfaces 144a can be engaged with the grooves 59, to restrict movement of the rotatable tube 101 with respect to the insertion section 16 along the longitudinal axis direction of the rotatable tube 101 (or the insertion section 16). In addition, when the locking surfaces 144a are engaged with the grooves 59, the locking surfaces 144a can move along the circumferential direction of the external circumferential surface of the insertion section 16, with rotation of the rotatable tube 101.

The internal circumferential surface (internal circumferential surface of the medium-diameter portion 143) of the rotatable tube 101 can be provided with bearing surfaces 62 on the distal end side and the proximal end side of the locking surface 144a, and the external circumferential surface (external circumferential surface of the receiving member 58) of the insertion section 16 can be provided with bearing surfaces 64 on the distal end side and the proximal end side of the grooves 59. The bearing surfaces 64 can be formed of circumferential surfaces, and the bearing surfaces 62 can be arc-shaped surfaces with a curvature radius that is set slightly larger than the curvature radius of the bearing surfaces 64 such that the bearing surfaces 62 are slidable with respect to the bearing surfaces 64. The bearing surfaces 62 and the bearing surfaces 64 can be configured to be mutually opposed and abut against each other when the rotatable tube 101 is inserted into the insertion section 16 and the locking surface 144A is engaged with the grooves 59. This structure restricts movement of the rotatable tube 101 in the radial direction of the insertion section 16. With rotation of the rotatable tube 101, the bearing surfaces 62 relatively move with respect to the bearing surfaces 64.

In the present embodiment, the position in which the grooves 59 formed in the receiving member 58 in the insertion section 16 are engaged with the locking surfaces 144a of the connectors 144 formed in the medium-diameter portion 143 of the connector body 140 in the connector 120 is located on a more distal end side in the longitudinal axis direction than the position in which the cover 60 is provided. The grooves 59 and the locking surface 144a in the second position of the connectors 144 can include a bearing mechanism 149 formed of the bearing surfaces 62 and the bearing surfaces 64. The bearing mechanism 149 can also provided on a more distal end side than a position in which the rotatable tube 101 receives the drive force from the drive mechanism 50 at the rotational engagement mechanism 180. The bearing mechanism 149 suppresses eccentricity of the rotation center from the central axis A1 of the insertion section 16 when the rotatable tube 101 is attached to the insertion section 16 and rotated around the longitudinal axis.

Next, a locking collar 160 of the overtube 100 will be described. FIG. 14 is a perspective view illustrating the locking collar 160 of the overtube 100. The locking collar 160 can be a hollow annular member, and configured with a size substantially being fitted onto the size of the medium-diameter portion 143 of the connector body 140. The locking collar 160 can be provided with an opening 161 to be engaged with a release button 145 of the connector body 140.

Next, a process to attach the overtube 100 to the endoscope 11 will be described.

The rotatable tube 101 of the overtube 100 can be inserted into the insertion section 16 from the distal end side of the insertion section 16 of the endoscope 11 into the proximal end side of the rotatable tube 101.

In the unlocked position as illustrated in FIGS. 15, 17 and 19, the connector 144 is in the stable equilibrium first position radially away from the longitudinal axis A2. Specifically, in the absence of an external force on the tab 144b, the hinge 144c biases the tab 144b to be in the stable equilibrium first position radially away from the longitudinal axis A2 to arrange the locking surface 144a at least a predetermined distance radially away from the longitudinal axis A2 to allow at least the distal portion of the insertion section 16 to be moved along the longitudinal axis A2 without contacting the locking surface 144a.

As illustrated in FIG. 5, the insertion section 16 is moved along the longitudinal axis A2 until the rollers 150 fixed to the large-diameter portion 141 of the connector body 140 abut against the protruding portion 60a formed by abutment of the drive roller 55 against the cover 60. Specifically, the rollers 150 abut against the drive roller 55 of the drive mechanism 50 arranged in the insertion section 16 via the cover 60.

Figure 18:
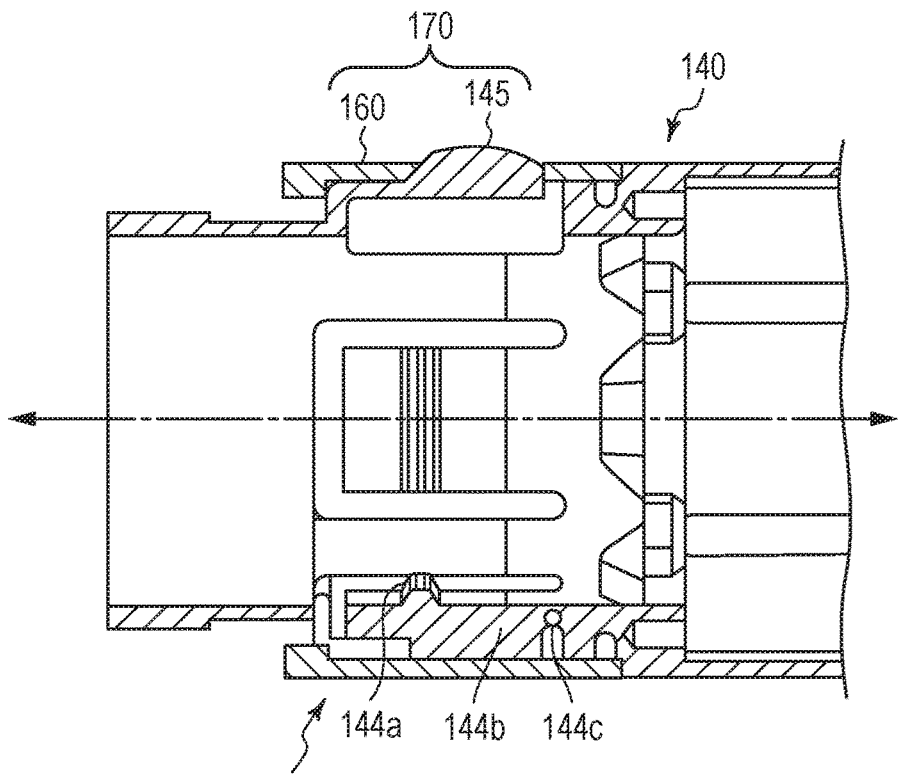
FIG. 18 is a cross-sectional view taken along line F-F in FIG. 16.
Figure 20:
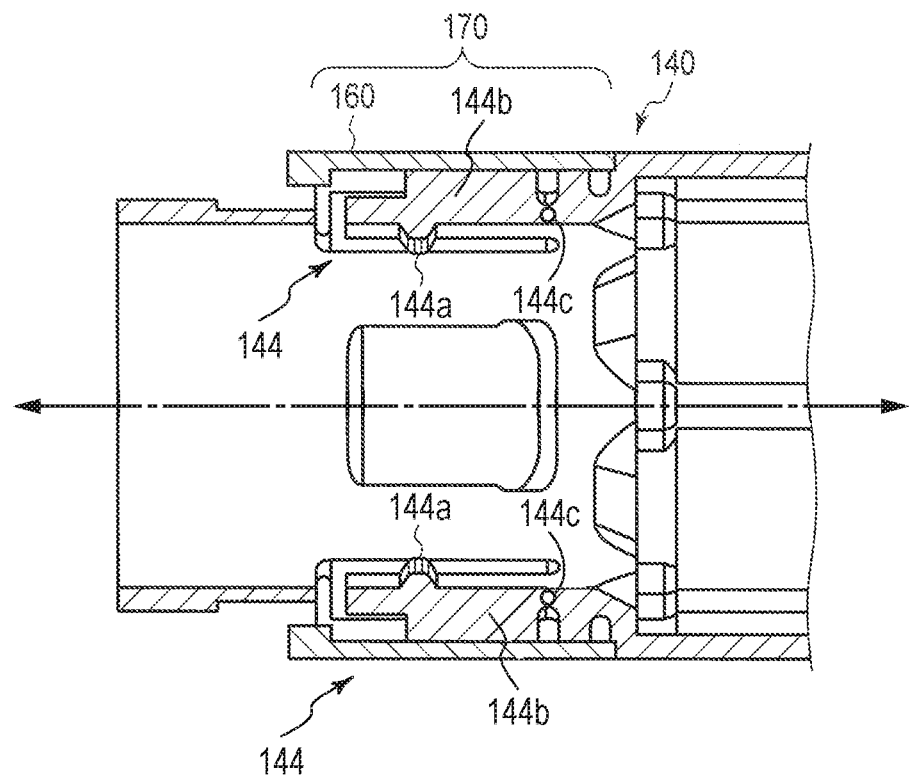
FIG. 20 is a cross-sectional view in a direction orthogonal to the cross section illustrated in FIG. 18.

FIG. 15 and FIG. 16 are top views of the connector body 140 and the locking collar 160 in an unlocked position and a locked position, respectively. FIG. 17 and FIG. 18 are a cross-sectional view taken along line E-E of FIG. 14, and a cross-sectional view taken along line F-F of FIG. 15, respectively. FIG. 19 and FIG. 20 are cross-sectional views in a direction orthogonal to the cross sections illustrated in FIG. 17 and FIG. 18, respectively. Specifically, FIG. 19 and FIG. 20 illustrate cross sections parallel with the central axis A1 and perpendicular to the cross sections of FIG. 17 and FIG. 18, respectively.

The locking collar 160 can be slidably attached to the external circumferential surface of the rotatable tube 101 such that the release button 145 of the medium-diameter portion 143 of the connector body 140 is aligned with the opening 161 of the locking collar 160 in the radial direction.

In the unlocked position illustrated in FIGS. 15, 17 and 19, the locking collar 160 is located on a more distal end side, for example, closer to the small-diameter portion 147, than the medium-diameter portion 143 of the connector body 140.

Further, in the unlocked position illustrated in FIGS. 15, 17 and 19, an external force can be applied to the connectors 144 to engage the locking surface 144a of the connectors 144 with the grooves 59 defined on the insertion section 16. Specifically, the external force is applied to the tab 144b that is biased by the hinge 144c to return to the stable equilibrium first position radially away from the longitudinal axis A2 such that the tab 144b is moved radially inward to the second position to engage the locking surfaces 144a of the connectors 144 with the grooves 59 defined on the insertion section 16.

In the state in which the locking surface 144a is engaged with the groove 59, the locking collar 160 can then be slid from the unlocked position towards the medium-diameter portion 143 of the connector body 140 to be in the locked position. The opening 161 of the locking collar 160 can be engaged with the release button 145 provided on the medium-diameter portion 143. Because the release button 145 is in a cantilever manner, when the locking collar 160 is moved onto the release button 145, the release button 145 is slightly flexed to be pushed down in the radial direction from the medium-diameter portion 143, and fitted and fixed into the opening 161. In the locked position, the locking surface 144a of the connector 144 is pressed by the locking collar 160 to move from the stable equilibrium first position to the second position to engage the locking surface 144a with the groove 59.

It is also contemplated that the tab 144b, in the stable equilibrium first position, can be angled with respect to the longitudinal axis A2 to permit the locking collar 160 to slide from the unlocked position towards the medium-diameter portion 143 of the connector body 140 to be in the locked position. As the locking collar 160 slides towards the locked position, the locking collar 160 engages the tab 144b to exert the force to move the tab 144b from the stable equilibrium first position to the second position to engage the locking surface 144a of the connector 144 with the grooves 59 defined on the insertion section 16.

Figure 22:
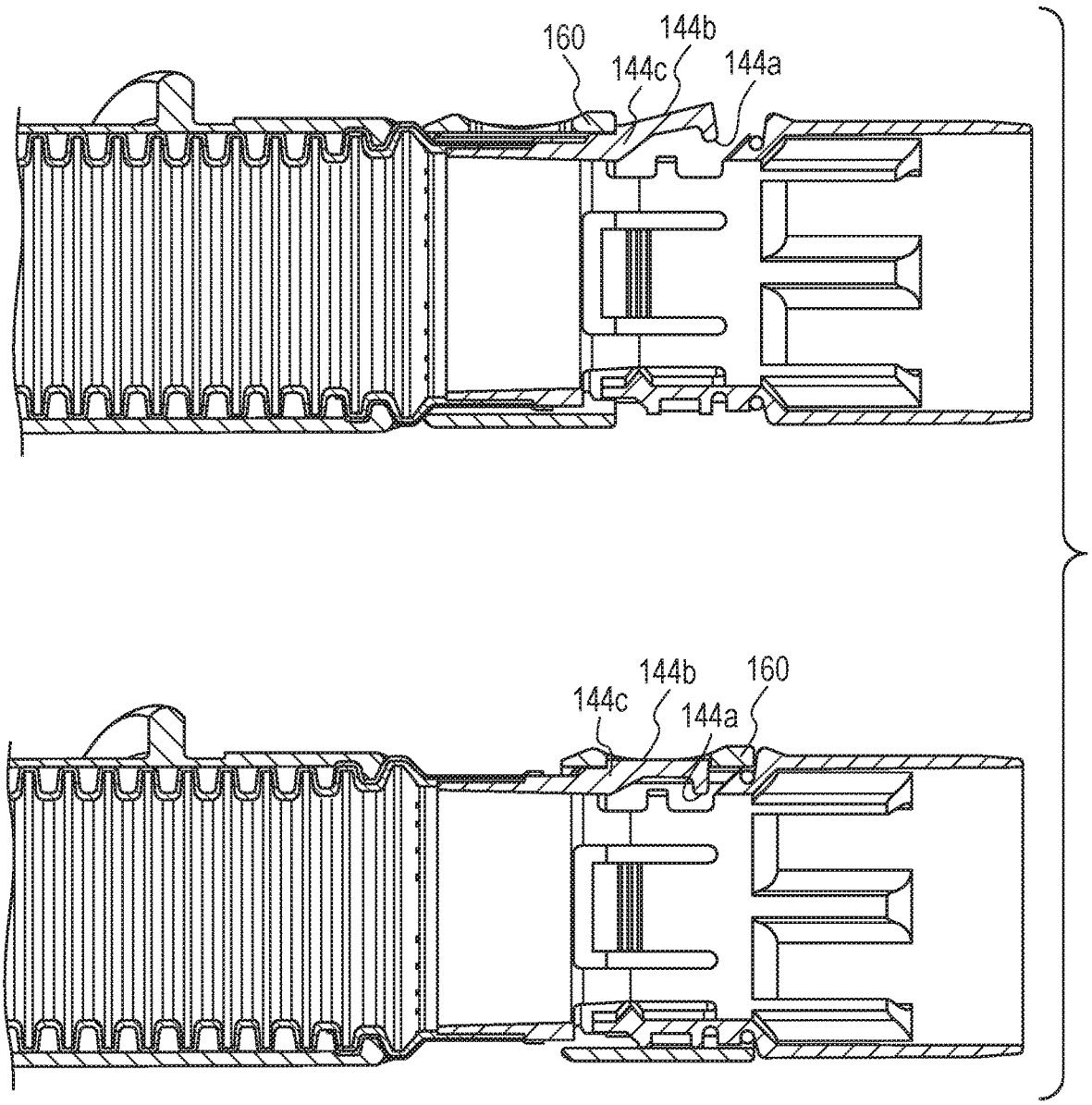
FIG. 22 is a top view illustrating another embodiment of the connector and the locking collar is an unlocked (top) configuration and a locked (bottom) configuration.

In the alternative configuration shown in FIG. 22, it is not necessary to first provide the external force to move the connectors 144 from the stable equilibrium first position to the second position, and then to slide the locking collar 160 from the unlocked position to the locked position to maintain the external force to thereby keep the connectors 144 in the second position. As shown in FIG. 22, as the locking collar 16 is slid from the unlocked position to the locked position, the locking collar 160 first abuts against a portion of the tab 144b closer to the hinge 144c than the locking surface 144a. As the locking collar 160 moves further towards the locked position, the locking collar 160 applies additional external force to pivot the tab 144b along the hinge 144c to move the locking surface 144a from the stable equilibrium first position to the second position to engage the locking surface 144a with the insertion section 16.

As a result of moving the locking surface 144A of the connector 144 from the stable equilibrium first position to the second position to engage the locking surface 144A with the insertion section 16, the rotatable tube 101 is prevented from moving in direction of the longitudinal axis A2 of the rotatable tube 101 (or the insertion section 16) with respect to the insertion section 16. In addition, because the bearing surfaces 66 and 68 are provided on the proximal end side of the drive roller 55, the bearing surfaces 66 and 68 further suppress eccentricity of the rotation center that causes shaking when the rotatable tube 101 is rotated around the longitudinal axis A2. Thus, the locking mechanism 170 can restrict an axial movement by engagement of the locking surface 144A and the groove 59 while allowing the connector body 140 to be rotated by the drive force.

Next, a process of detaching the overtube 100 from the endoscope 11 will be described.

When the overtube 100 is removed from the endoscope 11, the user pushes in the release button 145. Thereby, the release button 145 is moved inward in the radial direction, and detached from the opening 161 of the locking collar 160. Thereafter, by sliding the locking collar 160 toward the distal end side, the locking collar 160 is returned to the unlocked position, and the external force exerted on the connectors 144 is removed to allow the connectors 144 to be biased to return to the stable equilibrium first position radially further away from the longitudinal axis A2 than the second position to disengage the connectors 144 of the rotatable tube 101 from the insertion section 16. Thereafter, the rotatable tube 101 can be moved toward the distal end side with respect to the insertion section 16 to remove the rotatable tube 101 from the insertion section 16.

As the rotatable tube 101 is moved toward the distal end side with respect to the insertion section 16, since the connector 144 and in particular the locking surface 144a of the connector 144 is in the stable equilibrium first position, sufficient clearance is provided such that the connector 144 does not contact the external surface of the insertion section 16 as the insertion section 16 is removed from the rotatable tube 101.

In contrast to the overtube described in the "Background" section, in the present embodiment, the overtube 100 has connectors 144 that can maintain the stable equilibrium first position radially away from the longitudinal axis A2 of the rotatable tube 101. As discussed above, the stable equilibrium first position of the connectors 144 can provide sufficient clearance to avoid contact with the insertion section 16 as the insertion section 16 is moved along the longitudinal axis A2 through the lumen 111 of the rotatable tube 101 so that the connectors 144 do not contact or catch the external surface of the insertion section 16 during attachment and detachment of the overtube 100 to and from and insertion section 16. Accordingly, damage caused by contact of the connector 144 with the external surface of the insertion section 16 can be avoided.

Further, when the rotatable tube 101 is attached to the endoscope 11, for example, in the case where pawls provided on the overtube side are engaged with a flange located on a more proximal end side than the cover on the endoscope side to fix the rotatable tube 101 to the insertion section 16 in the radial direction, the pawls are required to move across the cover to be fixed. Because the pawls protrude inward in the radial direction of the rotatable tube 101, the pawls can catch and damage the cover as the pawls are moved across the cover.

In contrast, in the present embodiment, the connectors 144 provided on the tube main body 110 are arranged on a more distal end side in the longitudinal axis direction than the protruding portion 60a of the cover 60 covering the drive roller 55 of the drive mechanism 50 provided on the endoscope side. Thus, the connectors 144 do not pass over the protruding portion 60a of the cover 60 when the rotatable tube 101 is attached to the insertion section 16. This structure prevents the connectors 144 from catching the cover 60 and breaking or otherwise damaging the cover 60 during attachment and detachment of the rotatable tube 101.

The explanation described above takes the endoscope system 10 as the insertion apparatus to which the overtube 100 is attached, but the insertion apparatus is not limited to an endoscope. For example, the insertion apparatus may be an insertion apparatus to and from which a tube rotatable with respect to the insertion section is attachable and detachable, such as an operation manipulator. Accordingly, the introduction apparatus may be an apparatus including the rotation unit, and an insertion apparatus that is not limited to an endoscope and to and from which the rotation unit is attachable and detachable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An overtube attachable to an insertion section of an endoscope, the overtube comprising:
    a connector body defining a lumen through which the insertion section is insertable along a longitudinal axis extending through a distal opening and a proximal opening of the lumen; and
    a connecting mechanism comprising:
        a connector comprising a locking surface and a hinge configured to movably attach the locking surface to the connector body,
        wherein the connector is configured to have a resting open first position radially away from the longitudinal axis such that the locking surface does not contact the endoscope during insertion of the insertion section through the lumen of the connector body, and the locking surface is configured to be moved by a radial force to pivot along the hinge from the resting open first position to a second position radially closer to the longitudinal axis than the resting open first position,
        wherein, in the second position, the locking surface is configured to engage the endoscope to limit relative movement of the connector body and the insertion section along the longitudinal axis while allowing the connector body to be rotated by a drive force relative to the insertion section along the longitudinal axis, and
        wherein the hinge is configured to bias the locking surface to return to the resting open first position radially.

2. The overtube according to claim 1,
    wherein the connector comprises a tab comprising the locking surface,
    wherein the hinge is configured to bias the tab to return to the resting open first position radially away from the longitudinal axis, and
    wherein the tab is configured to be moved by the radial force to pivot along the hinge from the resting open first position to the second position to engage the locking surface with the endoscope to limit movement of the connector body relative to the insertion section along the longitudinal axis while allowing the connector body to rotate relative to the insertion section around the longitudinal axis.

3. The overtube according to claim 2,
    wherein the locking surface of the tab is formed by one of a convex protrusion and a concave groove, wherein the endoscope defines one of a concave groove to receive the convex protrusion of the locking surface of the tab and a convex protrusion to be received by the concave groove of the locking surface of the tab, and wherein the tab is configured to be moved by the radial force to pivot along the hinge from the resting open first position to the second position to engage the one of the convex protrusion and the concave groove forming the locking surface with the one of the concave groove and the convex protrusion defined by the endoscope, respectively, to engage the locking surface with the endoscope to limit movement of the connector body relative to the insertion section along the longitudinal axis while allowing the connector body to rotate relative to the insertion section around the longitudinal axis.

4. The overtube according to claim 1, wherein the endoscope comprises a drive mechanism arranged to the insertion section, wherein the drive mechanism is configured to provide the drive force, wherein the overtube comprises a rotational engagement mechanism attached to the connector body, wherein the rotational engagement mechanism is configured to receive the drive force from the drive mechanism of the endoscope to rotate the connector body relative to the insertion section around the longitudinal axis, and wherein in a configuration in which a distal end of the insertion section protrudes from the distal opening of the lumen of the connector body and the connector is in the second position and engaged with the endoscope, the connector is arranged closer to the distal opening of the lumen of the connector body along the longitudinal axis than the rotational engagement mechanism.

5. The overtube according to claim 1, wherein the connector comprises a tab comprising the locking surface.

6. The overtube according to claim 5, wherein the locking surface of the tab is formed by one of a convex protrusion and a concave groove, wherein the endoscope defines one of a concave groove to receive the convex protrusion of the locking surface of the tab and a convex protrusion to be received by the concave groove of the locking surface of the tab, and wherein the tab is configured to be moved by the radial force to pivot along the hinge from the resting open first position to the second position to engage the one of the convex protrusion and the concave groove forming the locking surface with the one of the concave groove and the convex protrusion defined by the endoscope, respectively, to engage the locking surface with the endoscope to limit movement of the connector body relative to the insertion section along the longitudinal axis while allowing the connector body to rotate relative to the insertion section around the longitudinal axis.

7. The overtube according to claim 1, wherein the connecting mechanism comprises:

a locking collar configured to move along the longitudinal axis from an unlocked position to a locked position to exert the radial force to move the locking surface from the resting open first position to the second position radially closer to the longitudinal axis than the resting open first position to engage the endoscope to limit relative movement of the connector body and the insertion section along the longitudinal axis while allowing the connector body and the insertion section to be rotated by the drive force relative to the insertion section around the longitudinal axis.

8. The overtube according to claim 1, further comprising a rotatable tube comprising:

a tube main body connected to the connector body and configured to be rotated together with the connector by the drive force relative to the insertion section along the longitudinal axis; and a spiral fin attached to or formed integrally with the tube main body on at least a portion of an external circumferential surface of the tube main body.

9. A system comprising:

an endoscope comprising an insertion section; and an overtube attachable to the insertion section of the endoscope, the overtube comprising:

a connector body defining a lumen through which the insertion section is insertable along a longitudinal axis extending through a distal opening and a proximal opening of the lumen; and a connecting mechanism comprising:

a connector comprising a locking surface and a hinge configured to movably attach the locking surface to the connector body, wherein the connector is configured to have a resting open first position radially away from the longitudinal axis such that the locking surface does not contact the endoscope during insertion of the insertion section through the lumen of the connector body, and the locking surface is configured to be moved by a radial force to pivot along the hinge from the resting open first position to a second position radially closer to the longitudinal axis than the resting open first position, wherein, in the second position, the locking surface is configured to engage the endoscope to limit relative movement of the connector body and the insertion section along the longitudinal axis while allowing the connector body to be rotated by a drive force relative to the insertion section around the longitudinal axis, and wherein the hinge is configured to bias the locking surface to return to the resting open first position radially.

10. The system according to claim 9, wherein the connector comprises a tab comprising the locking surface.

11. The system according to claim 10, wherein the locking surface of the tab is formed by one of a convex protrusion and a concave groove, wherein the endoscope defines one of a concave groove to receive the convex protrusion of the locking surface of the tab and a convex protrusion to be received by the concave groove of the locking surface of the tab, and wherein the tab is configured to be moved by the radial force to pivot along the hinge from the resting open first position to the second position to engage the one of the convex protrusion and the concave groove forming the locking surface with the one of the concave groove and the convex protrusion defined by the endoscope, respectively, to engage the locking surface with the endoscope to limit movement of the connector body relative to the insertion section along the longitudinal axis while allowing the connector body to rotate relative to the insertion section around the longitudinal axis.

12. The system according to claim 9,
wherein the connecting mechanism comprises:
a locking collar configured to move along the longitudinal axis from an unlocked position to a locked position to exert the radial force to move the connector from the resting open first position to the second position radially closer to the longitudinal axis than the resting open first position to engage the endoscope to limit relative movement of the connector body and the insertion section along the longitudinal axis while allowing the connector body and the insertion section to be rotated by the drive force relative to the insertion section around the longitudinal axis.

13. A method of operating a system comprising:
an endoscope comprising an insertion section; and
an overtube attachable to the insertion section of the endoscope, the overtube comprising:
a connector body defining a lumen through which the insertion section is insertable along a longitudinal axis extending through a distal opening and a proximal opening of the lumen; and
a connecting mechanism comprising:
a connector comprising a locking surface and a hinge configured to movably attach the locking surface to the connector body,
wherein the connector is configured to have a resting open first position radially away from the longitudinal axis such that the locking surface does not contact the endoscope during insertion of the insertion section through the lumen of the connector body, and the locking surface is configured to be moved by a radial force to pivot along the hinge from the resting open first position to a second position radially closer to the longitudinal axis than the resting open first position,
wherein, in the second position, the locking surface is configured to engage the endoscope to limit relative movement of the connector body and the insertion section along the longitudinal axis while allowing the connector body to be rotated by a drive force relative to the insertion section around the longitudinal axis, and
wherein the hinge is configured to bias the locking surface to return to the resting open first position radially,
wherein the method comprises:
inserting the insertion section of the endoscope through the lumen of the connector body along the longitudinal axis;
applying the radial force to the connector, against the bias, to move the locking surface, from the resting open first position radially away from the longitudinal axis to the second position, radially closer to the longitudinal axis than the resting open first position, to engage the endoscope to limit relative movement of the connector body and the insertion section along the longitudinal axis;
while the locking surface is in the second position through application of the radial force, applying the drive force to rotate the connector body relative to the insertion section along the longitudinal axis; and
removing the radial force applied to the locking surface, to allow the hinge to bias the locking surface to return from the second position to the resting open first position radially.

14. The method according to claim 13,
wherein the connecting mechanism comprises:
a locking collar configured to move along the longitudinal axis from an unlocked position to a locked position, and
wherein the method comprises:
moving the locking collar along the longitudinal axis from the unlocked position to the locked position to exert the radial force to move the locking surface from the resting open first position to the second position radially closer to the longitudinal axis than the resting open first position to engage the endoscope to limit relative movement of the connector body and the insertion section along the longitudinal axis; and
while the locking surface is in the second position through application of the radial force moving the locking collar to the locked position, applying the drive force to rotate the connector body relative to the insertion section along the longitudinal axis.

15. The overtube according to claim 1,
wherein the endoscope comprises a drive mechanism arranged to the insertion section, wherein
the drive mechanism is configured to provide the drive force,
wherein the overtube comprises a rotational engagement mechanism attached to the connector body,
wherein the rotational engagement mechanism is configured to receive the drive force from the drive mechanism of the endoscope to rotate the connector body relative to the insertion section around the longitudinal axis, and
wherein the hinge is arranged to be closer to the rotational engagement mechanism along the longitudinal axis than the locking surface, or the locking surface is arranged to be closer to the rotational engagement mechanism along the longitudinal axis than the hinge.

* * * * *